United States Patent [19]

Ashton et al.

[11] 4,017,504

[45] Apr. 12, 1977

[54] ANTIFUNGAL 1-SUBSTITUTED BENZIMIDAZOLES

[75] Inventors: Wallace T. Ashton, Clark; Edward F. Rogers, Middletown, both of N.J.

[73] Assignee: Merck & Co., Inc., Rahway, N.J.

[22] Filed: June 12, 1975

[21] Appl. No.: 586,439

[52] U.S. Cl. .............................. 260/302 H; 424/270
[51] Int. Cl.² ...................................... C07D 417/00
[58] Field of Search ................................ 260/302 H

[56] References Cited

UNITED STATES PATENTS

| | | | |
|---|---|---|---|
| 3,055,907 | 9/1962 | Brown et al. | 260/302 H |
| 3,928,372 | 12/1975 | Bochis et al. | 260/302 H |

*Primary Examiner*—R. J. Gallagher
*Attorney, Agent, or Firm*—David L. Rose; J. Jerome Behan

[57] ABSTRACT

New water soluble benzimidazoles with a high degree of stability, which are substituted at the 1-position with carboxyalkoxycarbonyl substituents and at the 2-position with a 4-thiazolyl group are effective fungicides and anthelmintics. The compounds as well as processes for their preparation are described along with antifungal and anthelmintic compositions for their use. The 1-position substituent is a carboxyalkoxycarbonyl group of from 3 to 11 carbon atoms including certain salts and derivatives of the carboxy group. The compounds are generally prepared by contacting a 1-unsubstituted benzimidazole with a protected carboxyalkoxycarbonyl chloride.

7 Claims, No Drawings

ANTIFUNGAL 1-SUBSTITUTED BENZIMIDAZOLES

DESCRIPTION OF THE PRIOR ART

Benzimidazoles having a heteroaryl radical in the 2-position have been described in the prior art as anthelmintic and antifungal agents. U.S. Pat. Nos. 3,017,415 and 3,370,957 are illustrative of this prior art. Although these materials are active antifungal agents, the search has continued for substances which are more potent and which are effective against fungi that are non-responsive or weakly responsive to the prior art compounds. In accordance with the present invention there is provided a group of highly active, broad-spectrum antifungal agents.

SUMMARY OF THE INVENTION

This invention relates to new compounds active as fungicides and anthelmintics, and to methods for their use. More specifically, this invention relates to 1-substituted benzimidazoles effective as fungicides which are water soluble and possess an unexpectedly high degree of stability. Still more particularly, the invention is directed to novel fungicides comprising compounds described as 1-carboxyalkoxycarbonyl-2-(4-thiazolyl)-benzimidazoles and salts and derivatives of said carboxy group; to compositions containing such compounds; and to methods of killing fungi or controlling their growth by the use of such compositions and compounds.

These fungicides are utilized for agricultural application, for instance, in preventing or minimizing fungus growth on plants, fruits, seeds or soil. These fungicidal agents or materials may also find use in medical thereapy such as the treatment of mycotic infections of man and animals.

Although many antifungal agents have been described and used heretofore in an effort to control fungi, none are entirely satisfactory and continued losses resulting from fungal attack make the problem of control a serious and lasting one.

It is an object of this invention to provide for novel compounds. It is a further object of this invention to provide novel antifungal agents, which possess a high degree of water solubility and stability. It is still a further object of this invention to provide new and improved methods of controlling the growth of fungi. Another object of this invention is to provide compositions useful in the control of fungi in or on plants and animals. It is still a further object of this invention to provide a method for controlling and killing fungi with synthetic organic chemicals. Further objects and advantages will become apparent from the following description of the invention.

As used in the description of our invention the expressions "fungicide" and "fungicidal" are intended to encompass control of fungi broadly so as to include the killing of fungi as well as the inhibiting of growth of fungi.

According to the present invention, it has now been found that certain 1-(carboxyalkoxycarbonyl)-benzimidazoles are higly effective antifungal agents. It will be appreciated by those skilled in the art that not all of the compounds defined hereinbelow have exactly the same degree of antifungal activity and it should also be understood that a particular compound of the invention will vary somewhat in activity depending upon the species of fungus subjected to its action.

DESCRIPTION OF THE INVENTION

The novel antifungal active compounds of this invention are best described by the following structural formula:

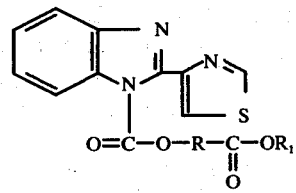

wherein R is a straight or branched alkylene of from 3 to 10 carbon atoms and $R_1$ is hydrogen, phenacyl, halophenacyl, an alkali metal cation, guanidinium or N-alkyl guanidinium.

The preferred compounds of this invention are realized when R is an alkylene of from 5 to 8 carbon atoms and $R_1$ is hydrogen or a cation of an alkali metal.

Examples of some of the compounds of this invention are the following:
1-(5-carboxy-n-pentyloxycarbonyl)-2-(4-thiazolyl)-benzimidazole sodium salt
1-(4-carboxy-n-butoxycarbonyl)-2-(4-thiazolyl)-benzimidazole
1-(6-carboxy-n-hexyloxycarbonyl)-2-(4-thiazolyl)-benzimidazole
1-(3-carboxy-n-propoxycarbonyl)-2-(4-thiazolyl)-benzimidazole
1-(7-carboxy-n-heptyloxycarbonyl)-2-(4-thiazoly)-benzimidazole potassium salt
1-(8-carboxy-n-octyloxycarbonyl)-2-(4-thiazolyl)-benzimidazole sodium salt
1-(10-carboxy-n-decyloxycarbonyl)-2-(4-thiazolyl)-benzimidazole
1-(1-carboxy-3-heptyloxycarbonyl)-2-(4-thiazolyl)-benzimidazole
1-(1-p-bromophenacyloxycarbonyl-3-heptyloxycarbonyl)-2-(4-thiazolyl)-benzimidazole
1-(8-p-bromophenacyloxycarbonyl-n-octyloxycarbonyl)-2-(4-thiazolyl)-benzimidazole The compounds of this invention may be employed in fungicidal treatment of seeds and crop seed pieces, plants, fruits, cereal grains, vegetables, nuts, bulbs, corms and tubers, flowers and ornamentals, turf, mushrooms, field crops and soils. These compounds are fungicidally effective against Ascomycetes, such as Erysiphe, Monilinia, Diplodia, Mycosphaerella, Septoria Sclerotinia, Sphaerotheca spp. and the like; Deuteromycetes, (Fungi imperfecti), such as Colletotrichum, Botrytis, Fusarium, Penicillium, Verticillium, Cercospora spp., Rhizoctonia, Sclerotium spp., and the like, and Basidiomycetes such as Ustilago spp., and the like.

The 1-substituted benzimidazoles of this invention are also effective against pathogenic fungi such as Trichophyton spp., Microsporum spp., Cryptococcus spp., and Hormodendrum spp.

It should be understood that the compounds may be utilized in diverse formulations, solid, including finely divided powders and granular materials as well as liquid, such as solutions, emulsions, suspensions, concentrates, emulsifiable concentrate, slurries and the like, depending upon the application intended and the formulation media desired.

Thus, it will be appreciated that compounds of this invention may be employed to form fungicidally active compositions containing such compounds as essentially active ingredients thereof, which compositions may also include finely divide dry or liquid diluents, extenders, fillers, conditioners and excipients, including various clays, diatomaceous earth, talc, and the like, or water and various organic liquids such as kerosene, benzene, toluene and other petroleum distillate fractions or mixtures thereof.

In general, the compounds of this invention are also effective in combatting superficial mycoses which attack and are an annoyance to humans such as the fungi which cause athletes foot and ringworm.

When the active agents are employed in preventing topical fungal growth one or more of the compounds may be uniformly distributed in a vehicle that is chemically compatible with the particular compound selected, non-inhibiting with respect to the action of the antifungal agent and essentially noninjurious to body tissue under the conditions of use.

It should be understood that the 1-substituted benzimidazoles of the invention may be used in combination one with the other as well as with other fungicidally active materials. For instance, a mixture of 1-substituted benzimidazoles and sulfur, dithiocarbamates, dichlorone, glyodin, dodine, oxine, captan, salicylanilide, dichlorophen, propionates and mineral oils can be used to given fungicidal effect when used in appropriate concentrations. It is quite clear, too, that the compounds defined according to Formula I above may be used in conjunction with effective antibacterial materials in appropriate instances so as to combine the action of each in such a situation as to be particularly useful, for instance, in applications where the presence of bacteria creates undesirable results alongside the detrimental action of fungi. Accordingly, a combination of antifungal and antibacterial agents will be useful in the preparation of germicidal soaps and in the production of cosmetics.

The growth of various fungi existing in soil is limited or terminated by the addition to the soil of minor quantities of the benzimidazole compounds described.

We have also found that the fungicides of the invention are effective against fungal diseases of plants, and may be effectively used either by direct contact with the foliage or systemically, by introduction through the roots.

With respect to the agricultural uses of the fungicides of this invention, the composition may be applied either pre-harvest or post-harvest, depending upon the particular plant, fruit, vegetable or other plant product being treated.

Pre-harvest treatment is used for sugar beets in the treatment of cercospora leaf spot (*Cercospora beticola*). In addition, these compounds are employed in the pre-harvest treatment of soybean pod rot complex, grey mold of grapes and various other fungal diseases of vegetables and field crops.

Post-harvest treatment of various fruits and vegetables with the compounds of this invention results in the successful treatment of many pathogenic fungi to which the fruit or vegetable is susceptible of infection. Examples are citrus fruits (penicillium ssp., stem end rot organisms and the like); pome fruit such as apples and pears (*Penicillium expansum, Gloeosporium perennans, Botrytis cinerea* and the like); crown rot complex of pathogens of bananas; potato storage and seed piece planting diseases as well as other fungal infections of other fruits and vegetables.

The compounds of this invention also find utility in the various fungi which attack ornamental plants and turf as well as in the treatment of seeds to prevent deterioration due to fungal infection while in storage and after planting.

The pre-harvest treatment of plants with the fungicides of this invention may be carried out using any of the methods known to those skilled in this art. The instant fungicides may be applied as a solution, suspension or dispersion in water in which the plant or the soil in which it is growing, or both, are thoroughly wetted with said aqueous solution, suspension or dispersion. The compounds may be intimately admixed with an inert solid carrier and "dusted" upon the plants. The solid mixture may also contain other necessary ingredients to insure that the composition remains dispersible in air and remains attached to the plant to which it is applied. Or the compounds may be dissolved, suspended or dispersed in a liquid carrier, such as non-phytotoxic oil or other non-aqueous liquid and sprayed directly upon the plant.

When the instant fungicides are used to treat turf and other grasses, the same application methods as above may be employed.

With post-harvest treatment of crops the fungicide may be applied at any time before consumption, preferably just after harvesting. For instance the antifungal compound may be applied during initial storage, before or after shipping or during final storage before consumption. The benzimidazoles of this invention may be utilized in a number of ways to protect the crop from fungal damage. The antifungal benzimidazoles may be applied directly to the crop as a solution emulsion, suspension, dispersion and the like, in which the carrier vehicle may be aqueous or non-aqueous in the form of a suitable, wax, oil, organic solvent and the like. The composition may also contain suitable dispersing agents stabilizing agents or other material to insure the uniform application of the benzimidazole derivative. Also the antifungal agent may be applied to the container or wrapper within which the crop is kept in order to prevent fungal damage. The antifungal agent is applied to the container or wrapper in carriers and waxes are known to those skilled in this art.

The 1-substituted compounds of the instant invention are prepared by reacting 1-unsubstituted-2-(4-thiazolyl)-benzimidazole with a protected carboxy alkoxy chloroformate, followed by the removal of the protecting group. The optimum protecting group is p-bromophenacyl as outlined in the following reaction scheme, however, other phenacyl protecting groups are acceptable such as unsubstituted phenacyl or other halo phenacyl groups:

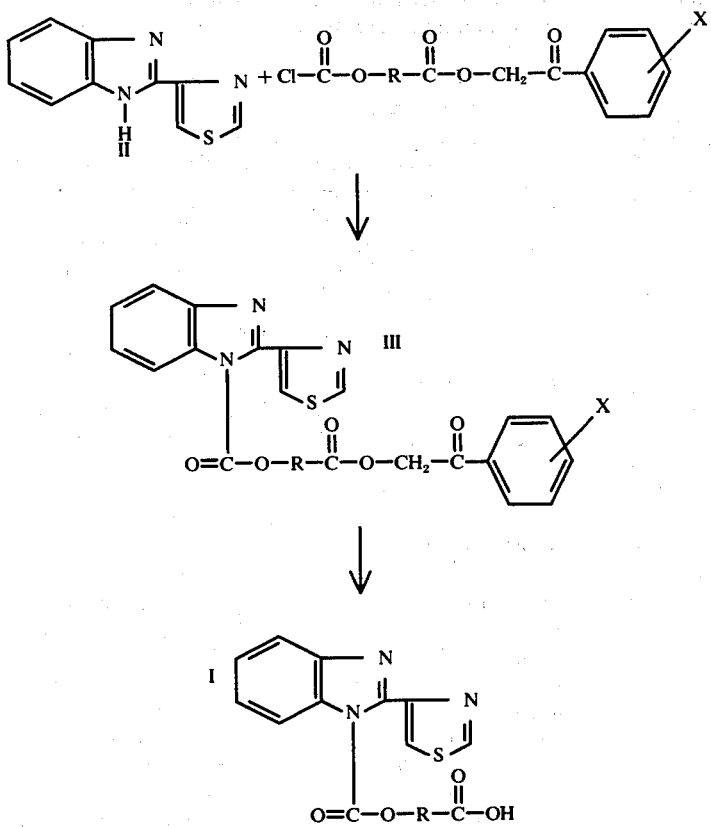

wherein R is as previously defined and X is hydrogen or halogen. Further reaction of the carboxy compound (I) will yield the metal or guanidinium salts.

The reaction of the 1-unsubstituted benzimidazole and the chloroformate is carried out in a solvent which is non-reactive to the chloroformate reagent. The reaction is generally complete in from ½ to 6 hours at from 10°–40° C. Appropriate solvents for this reaction are aprotic solvents, such as benzene, toluene, xylene, methylene chloride, acetonitrile, dimethyl formamide tetrahydrofuran and the like are suitable solvents for this process.

During the course of the reaction of the chloroformate reagent with the 1-unsubstituted benzimidazole, there is liberated one mole of hydrogen chloride. It is preferred to remove the liberated hydrogen chloride from the site of reaction by reacting it with a suitable base to form a salt. The base must be present at least in an amount equivalent to the hydrogen chloride being liberated. As bases, tertiary amines are preferred such as triloweralkylamines exemplified by triethylamine, methyldiethylamine and the like; aromatic amines such as N,N-diethylaniline and the like or heterocyclic amines such as pyridine and the like. Where the base is a liquid which is easily removable at the end of the reaction, the use of a separate solvent may be dispensed with and the base used in such an excess as to become the solvent itself. The technique is especially preferred when pyridine is the acid acceptor. The hydrogen chloride formed during the reaction reacts immediately with the base forming a salt which is removed at the end of the reaction by filtering, dissolving in water or some other technique known to those skilled in this art.

A variation of the above procedure is realized when a metal salt, preferably an alkali metal or alkaline earth metal salt of the 2-(4-thiazolyl)-benzimidazole is prepared prior to its reaction with the chlorformate reagent. Such a salt is prepared by using the alkali metal or alkaline earth metal hydride, hydroxide or loweralkoxide using methods well known in this art. By the use of such a salt of the benzimidazole, the reaction will produce rather than hydrogen chloride, an alkali metal or alkaline earth metal chloride. Thus, with this technique, the use of the base as described above is not needed and it is only necessary to remove the inorganic salt which formed directly during the course of the reaction.

The p-halophenacyl ester is reductively cleaved in order to prepare the free carboxylic compound of structure I. The preferred reduction conditions utilize a reactive metal such as zinc in acetic acid. Finely powdered zinc dust is preferred. The reaction is conducted at from 10° to 40° C. for from ½ to 6 hours and the product is isolated by techniques known to those skilled in this art.

The metal salts of Compound I are prepared by contacting the free carboxy compound of I with an aqueous solution of an alkali metal hydroxide, carbonate or bicarbonate. An alkali metal bicarbonate is preferred. The reaction is conducted in water optionally containing an organic cosolvent substantially at room temperature, although temperatures of from 10° to 40° C. are acceptable, and the reaction is complete in from ½ to 4 hours. The salt is isolated by techniques known to those skilled in this art.

The guanidinium and N-alkylguanidinium salts are prepared by metathesis from the metal salt of Compound I with a guanidinium or N-alkylguanidinium salt such as the hydrohalide or sulfate salt. The reaction is conducted in water at from 10° to 40° C., room temperature being the preferred temperature, however, and is complete in from 5 minutes to 1 hour. The combination of an organic cosolvent with the water is occasionally helpful in dissolving the starting materials and generally dioxane or loweralkanols are preferred for this purpose. The product is isolated by techniques known in this art.

The chloroformate starting materials are prepared in two steps from the metal salt, preferably the alkali metal salt of the corresponding hydroxy carboxylic acid, having the formula:

HO—R—COOM wherein R is as previously defined and M is the cation of a metal, preferably an alkali metal. This compound is reacted with a substituted or unsubstituted phenacyl halide in a polar aprotic solvent such as acetonitrile, tetrahydrofuran and the like. A catalytic amount of a solubilizing agent is generally employed to improve the solubility of the carboxylate salts. One of the "crown ethers" is generally preferred such as dicyclohexyl-18-crown-6. The reaction is conducted at from room temperature to the reflux temperature of the reaction mixture and is generally complete in from 15 minutes to 6 hours. The p-halophenacyl ester is recovered by techniques known to those skilled in this art.

The hydroxy group of the above recovered p-halophenacyl ester is treated with phosgene in order to prepare the chloroformate derivative. The reaction is run in a solvent and aprotic solvents are preferred such as aromatic hydrocarbons chlorinated hydrocarbons and the like as discussed above. The reaction is generally complete in from ½ to 2 hours when conducted at from −10° to 20° C. It is generally desireable to include in the reaction mixture an acid acceptor, such as an organic base, preferable pyridine, which is present in at least an amount equivalent to the acid liberated during the course of the reaction. The product is recovered by techniques known to those skilled in this art and the product reacted with the benzimidazole Compound II as described above.

The instant invention is further demonstrated by the following Examples, which Examples are provided for purposes of illustration and are not intended to limit the invention.

EXAMPLE 1

1-(5-Carboxypentyloxycarbonyl)-2-(4-thiazolyl)-benzimidazole

A. Potassium 6-hydroxycarproate

To a stirred mixture of 11.4 g. (100 mmoles) of caprolactone and 50 ml. of water is added 6.6 g. (100 mmoles) of 85% potassium hydroxide over a period of 5 minutes. The reaction mixture is stirred for 4 hours, filtered and evaporated to dryness in vacuo. The residue is suspended in 200 ml. of acetonitrile and stirred overnight resulting in complete crystallization. The solid is filtered, washed with acetonitrile and dried affording 16.4 g. of potassium 6-hydroxycaproate, m.p. 205°–207° C.

B. p-Bromophenacyl 6-hydroxycaproate

A mixture of 8.5 g. (50 mmoles) of potassium 6-hydroxycaproate, 13.9 g. (50 mmoles) of p-bromophenacyl bromide, 0.75 g. (2 mmoles) of dicyclohexyl-18-crown-6 in 500 ml. of acetonitrile is refluxed with stirring for 1 hour and stirred at room temperature overnight. The mixture is filtered and the filtrate evaporated to dryness in vacuo. The residual solid is recrystallized from benzene-hexane mixture affording 14.1 g. of p-bromophenacyl 6-hydroxycarproate, m.p. 79°–81° C.

C. p-Bromophenacyl 6-chloroformyloxycarpoate

To 60 ml. (70 mmoles) of 12.5% phosgene solution in benzene stirred in an ice bath under protection from moisture is added dropwise a solution of 11.5 g. (35 mmoles) of p-bormophenacyl 6-hydroxycaproate, 2.77 g. (35 mmoles) of pyridine in 50 ml. of methylene chloride over a period of 1 hour and 50 minutes. After the completion of the addition, stirring is continued in an ice bath for 3 hours. The mixture is purged with a stream of nitrogen to remove the excess phosgene and benzene is added to the residue. The insoluble pyridine hydrochloride is filtered, the filtrate concentrated to dryness in vacuo affording 14.05 g. of a light yellow residual oil which is used without further purificaation in the next step.

D. 1-[5-(p-Bromophenacyloxycarbonyl)pentyloxycarbonyl]-2-(4-thiazoly)-benzimidazole A solution of 14.0 g. (35 mmoles) of p-bormophenacyl 6-chloroformyloxycaproate in 15 ml. of methylene chloride is added dropwise with protection from moisture to a stirred suspension of 7.0 g. (35 mmoles) of 2-(4-thiazolyl)-benzimidazole in 25 ml. of pyridine over a period of 35 minutes. The reaction mixture is stirred for 1½ hours, filtered and the filtrate evaporated to dryness in vacuo. The residue is taken up in 100 ml. of methylene chloride and filtered. The filtrate is washed twice with 100 ml. of 0.5 N HCl containing ice, followed by 75 ml. of a saturated sodium bicarbonate solution containing 25 ml. of ice. The methylene chloride fraction is dried, treated with charcoal, filtered and evaporated to dryness in vacuo affording 17.1 g. of an oil which is used without further purification in the next step.

E. 1-(5-carboxypentyloxycarbonyl)-2-(4-thiazolyl)-benzimidazole

To a stirred solution of 11.1 g. (20 mmoles) of crude 1-[5-(p-bromophenacyloxycarbonyl)pentyloxycarbonyl]-2-(4-thiazolyl)-benzimidazole in 100 ml. of glacial acetic acid is added 6.5 g. (100 mmoles) of zinc dust in small portions over a period of 12 minutes. The reaction mixture is stirred for 30 minutes, filtered, the solid material washed with acetic acid and water. The combined filtrates are diluted with 1800 ml. of water and shaken with 1 liter of ethyl acetate. The ethyl acetate layer is washed with 3 additional 1800 ml. portions of water, dried over magnesium sulfate, filtered and evaporated to dryness in vacuo. The residue is washed 3 times with 30 ml. portions of ether and filtered affording 5.0 g. of 1-(5-carboxypentyloxycarbonyl)-2-(4-thiazolyl)-benzimidazole, m.p. 155°–156° C.

EXAMPLE 2

1-(1-Carboxy-3-heptyloxycarbonyl)-2-(4-thiazolyl)-benzimidazole

A. Potassium 4-hydroxyoctanoate

Following the procedure of Example 1A utilizing 7.1 g. (50 mmoles) of octanoic lactone, 25 ml. of water and 3.3 g. (50 mmoles) of 85% aqueous potassium hydroxide there is prepared 9.6 g. of potassium-4-hydroxyoctanoate.

B. p-Bromophenacyl 4-hydroxyoctanoate

Utilizing the process of Example 1B with 9.6 g. (45.8 mmoles) of the product of Example 2A, 13.5 g. (45.8 mmoles) of p-bromophenacyl bromide, 0.75 g. (2 mmoles) of dicyclohexyl-18-crown-6, and 485 ml. of acetonitrile, there is afforded 7.4 g. of p-bromophenacyl 4-hydroxyoctanoate m.p. 86.5°–87° C.

C. p-Bromophenacyl 4-chloroformyloxyoctanoate

Following the procedure of Example 1C utilizing 7.14 g. of the product of Example 2B in 1.58 g. of pyridine and 35 ml. of methylene chloride, with 34.5 ml. (40 mmoles) of 12.5% phosgene there is obtained 9.2 g. of p-bromophenacyl-4-chloroformyloxyoctanoate as an oil.

D. 1-(1-p-Bromophenacyloxycarbonyl-3-heptyloxycarbonyl)-2-(4-thiazolyl)-benzimidazole Following the procedure of Example 1D using 4.0 g (20 mmoles) of 2-(4-thiazolyl)-benzimidazole in 20 ml. of pyridine and 9.2 g. of the product of Example 2C there is obtained 8.3 g. of a viscous oil which is identified as 1-(1-p-bormophenacyloxycarbonyl-3-heptyloxycarbonyl)-2-(4-thiazolyl)-benzimidazole.

E. 1-(1-Carboxy-3-heptyloxycarbonyl)-2-(4-thiazolyl)-benzimidazole

The procedure of Example 1E is employed with 8.3 g. (14.2 mmoles) of the product of Example 2D in 70 ml. of glacial acetic acid and 4.65 g. (71 mmoles) of zinc dust, affording 3.55 g. of 1-(1-carboxy-3-heptyloxycarbonyl)-2-(4-thiazolyl)-benzimidazole m.p. 122°–125° C.

EXAMPLE 3

1-(5-Carboxypentyloxycarbonyl)-2-(4-thiazolyl)-benzimidazole sodium salt

To a solution of 0.5 g. (5 mmoles) of sodium bicarbonate in 12 ml. of water and 8 ml of dioxane is added 2.15 g. (6 mmoles) of 1-(5-carboxypentyloxycarbonyl)-2-(4-thiazolyl)-benzimidazole in small portions over a period of 15 minutes. The reaction mixture is stirred for 2.5 hours, filtered and the solution evaporated to dryness in vacuo. The viscous residual gum is triturated repeatedly with 40 ml. portions of acetonitrile until solidication occurs. The solid material is filtered and dried affording 2.14 g. of 1-(5-carboxypentyloxycarbonyl)-2-(4-thiazolyl)-benzimidazole sodium salt melting point softens in excess of 60° C. and decomposes in excess of 160° C.

EXAMPLE 4

1-(5-Carboxypentyloxycarbonyl)-2-(4-thiazolyl)-benzimidazole n-dodecylguanidinium salt A solution of 1.22 g. (3.0 mmoles) of 1-(5-carboxypentyloxycarbonyl)-2-(4-thiazolyl)-benzimidazole potassium salt in 10 ml. of water is added gradually to a stirred solution of 3.3 mmoles of n-dodecylguanidine hydrochloride in 20 ml. of water containing isopropanol. The product precipitates immediately and is stirred for 45 minutes, filtered and washed with water, methanol and acetone affording 1.19 g. of 1-(5-carboxypentyloxycarbonyl)-2-(4-thiazolyl)-benzimidazole n-dodecylguanidinium salt, When the compounds of this invention are employed in compositions useful for the destruction of fungi or the prevention of the growth of fungi, the active ingredient is present to an extent which depends greatly upon the method of application of the antifungal agent. Concentrations ranging from 500 to 5000 parts per million may be employed.

These compositions are applied to the plant, plant product, soil or other objects where fungal growth is present or suspected. In addition to applying these compositions to existing or suspected sites of fungal infection, it is very often useful to apply said compositions to plants, plant products or other objects where there is no fungal infection, however, from past experiences, fungal growth could reasonably be predicted. An example would be the treatment of fruits or vegetables which contain no fungal infection but which are to be placed in storage for prolonged periods or for shipment. In such situations, experience has shown that, left untreated, the fruits and vegetables will develop fungal infections. Treatment of such fruits and vegetables prior to storage will prevent the development of fungal infection.

The above concentrations of active ingredient are descriptive of those compositions which are to be applied directly to the site of fungal infection, suspected fungal infection or sites where fungal infection is predicted. However, it may be desired to provide for an intermediate composition of the compounds of this invention wherein the active ingredient is present to the extent of from 1 to 90% by weight. The remaining ingredients are auxilliary agents such as fillers, excipients, binders or other inert ingredients necessary to maintain the integrity of the composition. This higher concentration composition is further diluted, with the proper diluent for the particular contemplated use, prior to such use. The dilution brings the concentration of the active ingredient to that desired or necessary for the particular use to which the antifungal composition is to be put.

Compositions containing the active ingredient of structural Formula I are active against various fungi when such composition is applied to an area, plant or animal in which fungal growth is present, suspected or predicted.

In one such example in a greenhouse test an aqueous solution containing from 0.25 to 1% acetone and 7.5, 15 or 30 parts per million of the active compound was applied as a spray until runoff to young bean plants which had been previously inoculated with powdery mildew (*Erysiphe Polygoni*). Other plants were left untreated as controls. It is noted that field applications (as opposed to this laboatory situation) utilize a much higher level of active compound (200 to 5000 ppm). In the laboratory situation care is taken to thoroughly wet the entire surface of all the leaves of the plant. Since such techniques are too time consuming for field use, higher concentrations are employed. After 5 to 7 days the plants were evaluated on a scale of from 0 to 10 with 0 being no fungal infection and 10 being complete fungal infection. Scores of from 0 to 2 are considered as adequate control. In such tests the untreated plants were completely infected with the fungus while the instant compounds, at concentrations of 15 or 30 ppm. afforded adequate control.

When the compounds of this invention are intended for topical use such as in a cream or ointment, a base therefor is employed in which the active compound is present at a concentration of from 0.01% to 15% preferably from about 0.5% to 10% (percentages are by weight).

In addition to their antifungal activity, the compounds of this invention have significant activity as anthelmintics thus being useful in the treatment of helminthiasis in animals. The disease or group of diseases described generally as helminthiasis is due to infestation of the animal body with parasitic worms known as helminths. Helminthiasis is a prevalent and serious econimic problem in domesticated anismals such as swine, sheep, cattle, goats, dogs and poultry. Among the helminths, the group of worms described as nematodes causes widespread and often serious infection in various species of animals. Certain species of nematodes also lead to troublesome infections in humans, particularly in the tropical climates. The parasitic infections known as helminthiasis lead to anemia, malnutrition, weakness, weight loss, severe damage to the walls of the intestinal tract and, if left untreated, often result in death of the infected animals. The compounds of this invention have unexpectedly high activity against these helminths.

When used as anthelmintic agents, they may be administered orally in a unit dosage form such as a capsule, bolus, tablet or as a liquid drench. Alternatively, the anthelmintic compounds of this invention may be administered to animals by intraruminal, intramuscular and intratracheal injection, in which event the benzimidazole is dissolved or dispersed in a liquid carrier vehicle.

The optimum amount of the active agent to be employed for best results will, of course, depend upon the particular benzimidazole employed, the species of animal to be treated and the type and severity of helminth infection. Generally, good results are obtained with the compounds of this invention by the oral administration of from about 5 to 125 mg. per kg. of animal body weight, such total dose being given at one time or in divided doses over a relatively short period of time such as 1-2 days. With the preferred compounds of the invention, excellent control of helminthiasis is obtained in domesticated animals by administering from about 10 to 70 mg. per kg. of body weight in a single dose. The techniques for administering these materials to animals are known to those skilled in the veterinary field.

What is claimed is:

1. A compound having the formula:

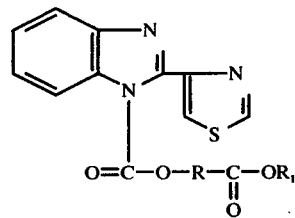

wherein R is a straight or branched alkylene of from 3 to 10 carbon atoms, and $R_1$ is hydrogen, phenacyl, halophenacyl, an alkali metal cation, guanidinium or N-dodecyl guanidinium.

2. The compound of claim 1 wherein $R_1$ is hydrogen or an alkali metal cation and R is a straight of branched alkylene of from 5 to 8 carbon atoms.

3. The compound of claim 2 wherein $R_1$ is hydrogen or the cations sodium or potassium.

4. The compound of claim 3 which is 1-(1-carboxy-3-heptyloxycarbonyl)-2-(4-thiazolyl)-benzimidazole.

5. The compound of claim 3 which is 1-(5-carboxy-n-pentyloxycarbonyl)-2-(4-thiazolyl)-benzimidazole sodium salt.

6. The compound of claim 1 which is 1-(5-carboxy-n-pentyloxycarbonyl)-2-(4-thiazolyl)-benzimidazole n-dodecylguanidinium salt.

7. The compound of claim 2 which is 1-(5-carboxy-n-pentyloxycarbonyl)-2-(4-thiazolyl)-benzimidazole potassium salt.

* * * * *